United States Patent [19]

Pontoglio et al.

[11] Patent Number: 4,883,893

[45] Date of Patent: Nov. 28, 1989

[54] PROCESS FOR THE CONTINUOUS PRODUCTION OF PHTALODINITRILE

[75] Inventors: Enrico Pontoglio, Brescia; Sandro Parodi, Nuvolento; Giancarlo Caretti, Brescia, all of Italy

[73] Assignee: Caffaro s.p.a. Societa per l'Industria Chimica Ed Elettro Chimica, Milan, Italy

[21] Appl. No.: 52,028

[22] Filed: May 19, 1987

[30] Foreign Application Priority Data

Jun. 24, 1986 [IT]  Italy ............................. 20884 A/86

[51] Int. Cl.$^4$ ........................................ C07C 120/04
[52] U.S. Cl. .................................................. 558/308
[58] Field of Search ........................................ 558/308

[56] References Cited

U.S. PATENT DOCUMENTS

2,177,619  10/1939  Nicodemus ..................... 558/308
3,070,621  12/1962  Lind ................................. 558/311

OTHER PUBLICATIONS

Chemical Abstracts, Abstract No. 134736z, vol. 87, No. 17, Oct. 24, 1977, p. 683.

*Primary Examiner*—Mary C. Lee
*Assistant Examiner*—Zinna Northington-Davis
*Attorney, Agent, or Firm*—Wolf, Greenfield & Sacks

[57] ABSTRACT

The present invention relates to a process for the continuous production of isophthalodinitrile or terephthalodinitrile by reaction in steam phase, on a fixed bed of a dehydration catalyst, of the correspondent bis(trichloromethyl)benzenes with ammonia optionally in the presence of aqueous steam.

8 Claims, No Drawings

PROCESS FOR THE CONTINUOUS PRODUCTION OF PHTALODINITRILE

BACKGROUND OF THE INVENTION

1. Field of the Invention

The present invention relates to a process for the production in continuous of phthalodinitrile. More particularly, the present invention relates to a process for the production in continuous of isophthalodinitrile or terephthalodinitrile by reaction of the respective bis(trichloromethyl)benzenes with ammonia in stream phase on a fixed bed of a dehydration catalyst. Optionally this reaction is carried out in the presence of aqueous steam.

2. Prior Art

Dinitriles of the acrylic acids can only be prepared by complex chemical methods or adopting sophisticated and expensive equipment. The classical method, from carboxylic acids, by reaction with ammonia in steam phase on dehydration catalysts, is often not easily applicable due to the chemical-phisical characteristics of the starting acids. In fact many solid aromatic acids, such as for example, phthalic acids, are difficult to vaporize, melt at high temperatures and already at these temperatures they begin to decompose developing carbon dioxide.

Consequently, attempts have been made to overcome these difficulties in different ways, for example dispersing the pulverized aromatic acid in a stream of inert gas at a temperature below its melting point, mixing it with a very hot ammonia stream, and conveying the vaporized reaction products on a dehydration bed. This method, claimed in U.S. Pat. No. 3,070,621, which avoids the melting of the aromatic acid, considerably reduces the decomposition phenomena and therefore the forming of deposits and crusts on the reactor walls, especially in that zone used as vaporizer. Anyway it is evident that this results considerable installation difficulties and it is therefore clear why successively other ways were tried, such as for instance the use of phthalic acid derivates, which vaporize more easily: for example, ammonium salts, diamides and above all esters of such acids, wherein the alkyl chain contains from 1 to 4 carbon atoms. Thus, for example, DTAS 1,279,020 claims the preparation of aromatic nitriles from methyl esters of the correspondent acids: these processes, if on the one hand simplify the installations, on the other hand raise the new problem of the precursor production, which precursors are not easily available on commercial and industrial scale.

Only in the last 20 years new processes of ammono-oxidation were industrially developed, which consist in reacting mixtures of aromatic hydrocarbon containing an alkyl chain, oxygen or air, and ammonia at high temperatures on suitable vanadium, tungsten etc. catalysts. However, these processes require high technologies, suited to effect the reactions in steam phase, on fluidized beds; separation and recycle of the unreacted compounds or of the reaction intermedies, the use of particular and sophisticated catalysts, and in addition plants of considerable size are needed, which require high capital investements.

The Applicant has claimed in its patent application No. 20077 A/86 filed on Apr. 14, 1986 a process for the production in continuous of isophthalodinitrile and terephthalodinitrile by amidation and simultaneous dehydration of the respective acid chlorides in steam phase on a fixed bed of a dehydration catalyst.

Chlorides of phthalic acids are commercially available in industrial quantities or can be obtained according to different kinds of synthesis. For instance a classical way is the reaction of the corresponding aromatic acids with chlorinating agents such as thionyl chloride, phosphorous oxychloride, phosgene etc. A more convenient synthesis involves the photochlorination of the respective xylenes and the subsequent partial hydrolysis of the resultant $\alpha,\alpha,\alpha,\alpha',\alpha',\alpha'$, hexachloroxylenes by means of $H_2O$ or $CH_3OH$ (see U.S. Pat. No. 3,835,187) or the melting with equimolecular quantities of the corresponding aromatic acids (see British Pat. No. 946,491).

SUMMARY OF THE INVENTION

The Applicant has now surprisingly found, and this is an object of the present invention, that it is possible to obtain phthalodinitrile by adopting, as raw materials, directly the $\alpha,\alpha,\alpha,\alpha',\alpha',\alpha'$, hexachloroxylenes.

More particularly it has been found that it is possible to obtain in continuous isophthalodinitrile or terephthalodinitrile by reacting, in steam phase on a fixed bed of a dehydration catalyst, the correspondent bis(trichloromethyl)benzenes, optionally in the presence of aqueous steam.

Therefore it is an object of the present invention a process for the preparation in continuous of compounds of formula (I)

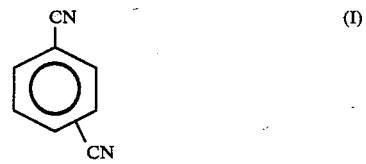

by reacting a compound of formula (II)

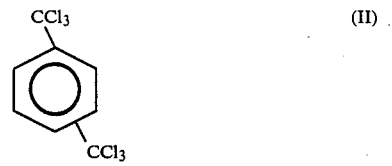

with ammonia vapors in the presence of a dehydration catalyst, characterized in that:

(a)—the compounds of formula (II) are reacted in vapor form;

(b)—the reaction is carried out in absence of solvent; and (c)—the catalyst is in form of a fixed bed wherein the temperature ranges from 300° to 450° C.

According to the invention, the reaction is particularly surprising as the production of nitriles and trichloromethylbenzenes according to the scheme:

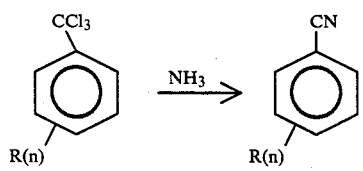

wherein R is an hydrogen or halogen atom or an alkyl alkoxy group, NO₂ etc. and n=1-2 is known and has been successfully used only for aromatic compounds with only a trichloromethyl group (benzotrichlorides) operating in solution and in autoclave (Japan Patent; DTOS 2,550,261).

The reaction according to the present invention, can be carried out in the presence of aqueous vapor.

The used row materials, namely α,α,α,α',α',α', hexachloroxylenes are solid, low melting and easy vaporizable compounds; therefore taking advantage of these favorable characteristics their vapors, optionally diluted in an inert gaseous medium such as for example air or nitrogen, preferably pre-heated, are sent through a fixed bed, comprising a dehydration catalyst maintained at the desired temperature by means of a suitable outer heating. Separately and contemporaneously ammonia gas and optionally aqueous vapor, pre-heated at temperatures very close to the reaction temperatures (for example from 200° to 500° C., preferably from 250° to 350° C.) is introduced into the bed.

Due to the high temperature and due to the presence of the catalyst, reactions occur which bring to the production of phthalodinitrile and ammonium chloride vapors, the latter, due to the high temperature, substantially dissociated in hydrogen chloride, and ammonia. The reacting gases and vapors coming from the reactor are then cooled and in this way a mixture of phthalodinitrile and ammonium chloride is recovered.

From this powder mixture, by an abundant water wash, the insoluble dinitrile is recovered. In alternative, the reaction gases can be directly and continuously removed by means of water and the resulting suspension can be directly filtered.

The obtained phthalodinitriles are products of very high purity generally with titles higher than 98%.

The yields based on the bis(trichloromethyl)benzene are ≧90% in case of terephthalodinitrile and ≧80% in case of isophthalodinitrile.

In absence of aqueous vapour in the reaction on the catlytic bed, lower purity and yields are obtained.

The dehydration catalysts suitable to be used are known in the art and have been described in some papers, for example in "Catalysis" by Berkman, Morrel and Egloff.

For the considered purposes, some catalysts, such as activated alumina, silica gel and thorium dioxide (torina), which are stable at the process temperatures, have proved to be particularly satisfactory. Other catalysts include zirconium, beryllium, tungsten and vanadium oxides, basic aluminum phosphate, basic aluminum sulphate and phosphoric acid; as support for the catalyst Alundum can, for example, be used.

The molar ratio between ammonia and bis(trichloromethyl)benzene can be included in rather wide ranges, for example between 2 and 100, preferably between 10 and 15.

The excess of unreacted ammonia is suitably recovered and optionally used again after the separation of the reaction products by a suitable recycle system.

The reaction is carried out preferably in the presence of in an inert gas, the presence of which helps the removal from the catalytic bed of the reaction products, especially ammonium chloride which is in considerably quantities.

DESCRIPTION OF THE PREFERRED EMBODIMENTS

The herein enclosed examples are given to better illustrate the process without however having a limitative character.

EXAMPLE I 1,3-bis(trichloromethyl)benzene (0.0380 M/h) vaporized in a nitrogen stream (0.615 M/h) is fed at the bottom of a fixed bed reactor, having a 4 cm. diameter and a 20 cm. length, loaded with 161.5 (about 206 cc) of activated aluminum in form of microspheres having a diameter ranging from 1.5 to 2 mm. Contemporaneously a mixture of ammonia gas (0.6037 M/h), aqueous vapour (0.1376 M/h) and nitrogen (1.889 M/h) is sent to the bottom of the catalyst layer. The two feed streams are suitably pre-heated before the mixing, in order to maintain the catalytic bed, outwardly heated by resistors, at the temperature of about 350° C.

The gases and vapors from the top of the reactor are cooled in a tank vessel at room temperature. There the isophthalodinitrile and the ammonium chloride desublimate as a crystalline powder, while the escaping gases and vapors (N₂, NH₃H₂O) are sent to a water spray removing system.

The reaction is carried out in continuous for seven hours and the collected solid, weights after an abundant and accurate washing with water to remove the formed ammonium chloride, and after having been filtered and dried in an oven at 70° C., weights 28.5 g.

The I.R. and gas-chromatographic analysis confirm that it is isophthalodinitrile having a high purity degree (99.8%).

The reaction yield based on 1.3-bis(trichloromethyl)benzene is therefore 82%.

EXAMPLE II

Vapors of 1.3-bis(trichloromethyl)benzene, (0.0503 M/h) gaseous ammonia (2.672 M/h), and nitrogen (0.615 M/h) are sent, at the reacting temperature of about 345° C., to the bottom of the same previously descriptive reactor and with the same modalities.

After a reaction period of six hours and 23 minutes, 30.3 g of isophthalodinitrile are collected. Title and molecular yield are respectively 64.6% and 47.6%.

EXAMPLE III

With the same modalities and equipment of example I vapours of 1.4-bis(trichloromethyl)benzene (0.0335 M/h), gaseous ammonia (0.9243 M/h), aqueous vapor (0.1578 M/h) and nitrogen (2.228 M/h) at the reacting temperature of about 350° C. are fed in continuous for 7 hours.

At the end 27.61 g are after the usual purification operations 27.61 g are collected which the I.R. and gas-chromatographic analysis confirm to be terephthalodinitrile at 99%.

The calculated yield is therefore 91% in respect to 1.4-bis(trichloromethyl)benzene.

We claim:
1. Process for the preparation of compounds of formula (I)

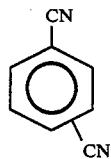 (I)

by reacting a compound of formula (II)

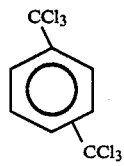 (II)

with ammonia vapours in the presence of a dehydration catalyst, wherein:

(a) the compounds of formula (II) are reacted in the form of vapours;

(b) the reaction is effected in the absence of solvent; and (c) the catalyst is in the form of a fixed bed, wherein the temperatures ranges from 300° to 450° C.

2. Process according to claim 1, wherein it is carried out in the presence of aqueous vapour.

3. Process according to claim 1, wherein the ammonia is used in a molar ratio in respect to bis(trichloromethyl)benzene comprised between 2 and 100.

4. Process according to claim 1, wherein the ammonia vapours are pre-heated.

5. Process according to claim 1, wherein the compounds of formula (II) are conveyed by a stream of inert gas.

6. Process according to claim 1, wherein the compound of formula (I) and any NH$_4$Cl formed are recovered in an appropriate condenser, then the dinitrile is isolated and purified by washing with water.

7. Process according to claim 1, wherein the catalytic bed consists of activated alumina, thorium oxide and silica gel.

8. Process according to claim 1, wherein the catalytic bed consists of activated alumina, thorium oxide or silica gel.

* * * * *